United States Patent [19]
Allnutt et al.

[11] Patent Number: 6,027,900
[45] Date of Patent: Feb. 22, 2000

[54] METHODS AND TOOLS FOR TRANSFORMATION OF EUKARYOTIC ALGAE

[75] Inventors: F. C. Thomas Allnutt, Port Deposit; David J. Kyle, Catonsville, both of Md.; Arthur R. Grossman, Mountain View, Calif.; Kirk R. Apt, Columbia, Md.

[73] Assignees: Carnegie Institution of Washington, Washington, D.C.; Martek Biosciences Corporation, Columbia, Md.

[21] Appl. No.: 09/155,972

[22] PCT Filed: Apr. 11, 1997

[86] PCT No.: PCT/US97/06021

§ 371 Date: Oct. 9, 1998

§ 102(e) Date: Oct. 9, 1998

[87] PCT Pub. No.: WO97/39106

PCT Pub. Date: Oct. 23, 1997

Related U.S. Application Data

[60] Provisional application No. 60/014,634, Apr. 12, 1996.

[51] Int. Cl.[7] .................................................. C12Q 1/68
[52] U.S. Cl. ..................... 435/6; 435/69.1; 435/320.1; 435/257.2; 536/23.4; 536/24.1
[58] Field of Search ................ 435/6, 69.1, 320.1, 435/257.2; 536/23.4, 24.1

[56] References Cited

U.S. PATENT DOCUMENTS

| | | | |
|---|---|---|---|
| 5,100,792 | 3/1992 | Sanford et al. | 435/69.1 |
| 5,661,017 | 8/1997 | Dunahay et al. | 435/69.1 |

FOREIGN PATENT DOCUMENTS

| | | |
|---|---|---|
| 0108580 | 5/1984 | European Pat. Off. . |
| 3076583 | 4/1991 | Japan . |
| WO 9739106 | 10/1997 | WIPO . |

OTHER PUBLICATIONS

Adhikary et al., "Utilization of Organic Substrates by Two Filamentous Cyanobacteria Under Various Growth Conditions," *Acta Microbiologica Hungarica* 35(2): 101–106 (1988).

Amla et al., "Metabolic changes associated with cyanophage N–1 infection of the cyanobacterium *Nostoc muscorum*," *Archives of Microbiology* 148(4): 321–327 (1987).

Beuf et al., "A protein involved in co–ordinated regulation of inorganic carbon and glucose metabolism in the facultative photoautotropic cyanobacterium *Synechocystis* PCC6803," *Plant Molecula Biology* 25: 855–864 (1994).

Broedel et al., "Growth–phase–dependent induction of 6–phosphogluconate dehydrogenase and glucose 6–phosphate dehydrogenase in the cyanobacterium *Synechococcus* sp. PCC7942," *Gene* 109: 71–79 (1991).

Charng et al., "Structure–function relationships of cyanobacterial ADP–glucose pyrophosphorylase," *The Journal of Biological Chemistry* 269(39): 24107–24113 (1994).

Charng et al., "Mutagenesis of an amino acid residue in the activator–binding site of cyanobacterial ADP–glucose pyrophosphorylase causes alteration in activator specificity," *Archives of Biochemistry and Biophysics* 318(2): 476–480 (1995).

Cossar et al., "Thioredoxin as a modulator of glucose–6–phosphate dehydrogenase in a $N_2$–fixing cyanobacterium," *Journal of General Microbiology* 130: 991–998 (1984).

Dunahay et al., "Genetic transformation of the diatoms *Cyclotella cryptica* and *Navicula saprophila*," *J.Phycol.* 31: 1004–1012 (1995).

Dunahay et al., "Genetic engineering of microalgae for fuel production," *Applied Biochemistry and Biotechnology* 34/35: 331–339 (1992).

Kirk et al., "Stable nuclear transformation of the diatom *Phaeodactylum tricornutum*," *Mol. Gen. Genet.* 252: 572–579 (1996).

Matsuoka et al., "Expression of photosynthetic genes from the $C_4$ plant, maize, in tobacco," *Mol. Gen. Genet* 225:411–419 (1991).

Stevens et al., "Development of a dominant selectable market for nuclear transformation of *Chlamydomonas reinhardtii*," *Journal of Experimental Botany* 46, supplement, p. 37 (1995).

Tandeau de Marsac, "Cyanobacterial genetic tools: curent status," *Meth Enzymol* 167: 831–847 (1988).

*Primary Examiner*—James Ketter
*Attorney, Agent, or Firm*—Baker & Botts, L.L.P.

[57] ABSTRACT

Genetic fusions for use in genetic engineering of eukaryotic algae employ a promoter from a light harvesting protein fused to a protein of interest. The fusions can be introduced and selected using an antibiotic resistance determinant. One gene useful for such selection is the sh ble gene encoding a bleomycin binding protein.

22 Claims, 2 Drawing Sheets

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:Ble-R5
      primer containing a portion of the sh ble gene

<400> SEQUENCE: 1
ctagatatca agatggccaa gttgaccagt                                    30

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:Ble-H3
      primer containing a portion of the sh ble gene

<400> SEQUENCE: 2
gataagcttc agtcctgctc ctcgg                                         25

METHODS AND TOOLS FOR TRANSFORMATION OF EUKARYOTIC ALGAE

This application claims benefit of Provisional Application 60/104,634 filed Apr. 12, 1996.

BACKGROUND OF THE INVENTION

The importance of algae as a resource for new products in both the present and the future cannot be overemphasized (Cannell, 1990, "Algal Biotechnology," *Applied Biochemistry and Biotechnolgy*, 26, 85–106). Algae have the potential to be used in high density photobioreactors (Lee et al., 1994, "High density algal photobioreactors using light emitting diodes". *Biotech. Bioengineering*, 44, 1161–1167; Chaumont, 1990, "Biotechnology of algal biomass production. A review of systems for outdoor mass culture," *J Appl. Phycology* 5, 593–604), bioreactors for sewage (Sawayama et al., 1994, "Continuous cultures of hydrocarbon-rich microalga *Botryococcus braunii* in secondarily treated sewage," *Appl. Micro. Biotech.*, 41, 729–731; Lincoln 1993, *Bulletin De L'institut Oceangraphique (Monaco)*, 12, 109–115) and waste water treatments, elimination of heavy metals from contaminated water (Wilkinson, 1989, "Mercury accumulation and volatilization in immobilized algal cell systems," *Biotech. Letters*, 11, 861–864), the production of β-carotene (Yamaoka, 1994, *Seibutsu-Kogaku Kaishi*, 72, 111–114) and pharmaceutical compounds (Cannell, 1990), as nutritional supplements for both humans and animals (Becker, 1993, "Development of Spirulina research in a developing country: India". *Bulletin De L'institut Oceanographique (Monaco)*, 12, 141–155) and for the production of other compounds of nutritional value. None of these areas has been adequately explored and exploited at this time. The full potential of algae can only be fully developed with an increase in our ability to genetically tailor algae for specific purposes. Genetic engineering can potentially be used to improve the productivity of algae. Unfortunately, until recently most algae were refractory to any type of genetic manipulation, this especially true for the eukaryotic algae. The molecular biological manipulation of algal systems has thus seriously lagged behind other systems. Many of the techniques that have been developed for the introduction of DNA into bacterial, yeast, insect and animal cells have not been adapted to algal systems.

Algal synthesis of valuable molecules on a large scale requires precise methods to enhance the quantity and quality of the product being made, either by changing what is being produced or producing more of a desirable substance. The only way this can be accomplished, in an economical manner, is by molecular biological manipulation. Previous academic investigations used a small number model algal species that have little possible use in a production mode (i.e., *Chlamydomonas reinhartii* and *Synechococcus sp.* PCC 7942), their choice dictated by special characteristics that have little to do with commercial utility.

Thus, there is a need for new methods and tools for use in the genetic engineering of eukaryotic algae in order to manufacture products.

SUMMARY OF THE INVENTION

It is an object of the invention to provide a genetic fusion for selection or expression in algae.

It is another object of the invention to provide DNA vectors and cells comprising the genetic fusions.

It is yet another object of the invention to provide methods of transforming eukaryotic algae.

These and other objects of the invention are provided by one or more of the following embodiments. In one embodiment of the invention, a genetic fusion is provided. The genetic fusion consists of a promoter of a photosynthetic algal light harvesting protein 5' and fused to a coding sequence of one or more additional proteins.

In another embodiment of the invention a method of transforming eukaryotic algae is provided. The method comprises the steps of:

introducing DNA to eukaryotic algae, wherein the DNA contains a zeocin resistance determinant; and selecting for eukaryotic algae transformants by culturing in a medium comprising between about 10 and about 35 g/L salt and a concentration of zeocin or phleomycin which is inhibitory to untransformed eukaryotic algae.

The present inventors have discovered that eukaryotic algae can be transformed with DNA using zeocin resistance as a selectable marker for transformants. Use of this and related antibiotics is desirable because they can be used in the presence of salt water; other antibiotics and herbicides tested are not effective in the presence of concentrations of salt present in natural salt water. The present inventors have also discovered that promoters for genes encoding light harvesting proteins can be used to drive expression of exogenous DNA introduced into algae. Because light harvesting proteins are expressed abundantly in photosynthetic algae, their promoters drive robust expression. Based on these discoveries, the present invention provides various embodiments which will be described in more detail below, and these embodiments, alone or in combination provide the art with means to genetically manipulate algae and various marine organisms to modify their properties in desirable ways.

DETAILED DESCRIPTION OF THE PREFERRED EMBODIMENTS

Definitions

Figure 1:
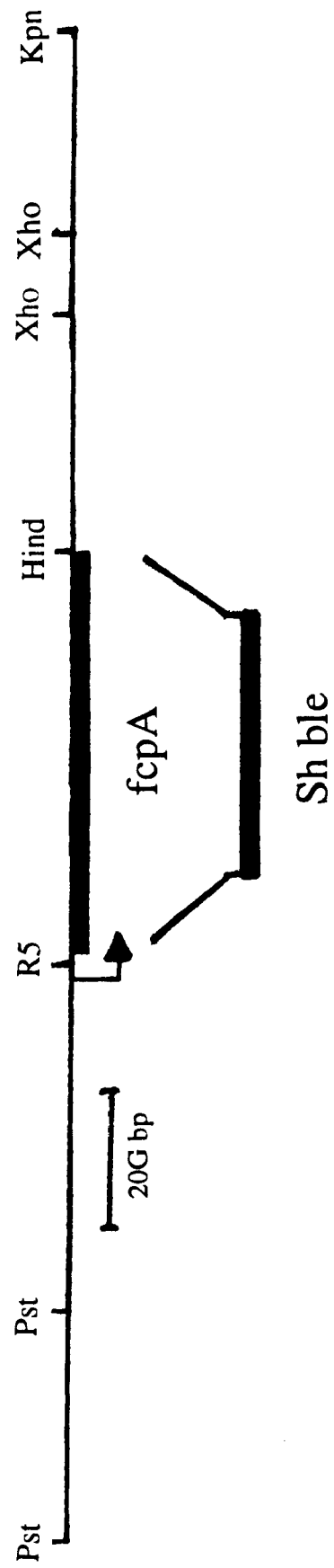
FIG. 1 presents a map of restriction enzyme sites in the fcp/ble gene fusion cassette. The coding region of the sh ble gene was inserted between the EcoRV and HindIII sites of the *P. tricornutum* fcpA gene. The transcription start site of the endogenous fcpA is marked by an arrow. The entire cassette is inserted into Bluescript SK- and designated pfcp/ble.

In describing the present invention, the following terminology is used in accordance with the definitions set out below.

A "chimeric DNA" is an identifiable segment of DNA within a larger DNA molecule that is not found in association with the larger molecule in nature. Thus, when the chimeric DNA encodes a protein segment, the segment coding sequence will be flanked by DNA that does not flank the coding sequence in any naturally occurring genome. Allelic variations or naturally occurring mutational events do not give rise to a chimeric DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide in vivo. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. A coding sequence is "under the control" of the promoter sequence in a cell when RNA polymerase which binds the promoter sequence transcribes the coding sequence into mRNA which is then in turn translated into the protein encoded by the coding sequence. For purposes of defining the present invention, the promoter sequence is bounded at its 3' terminus by the translation start codon of a coding sequence and extends upstream (5' direction) to include at least the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Promoters will usually contain additional consensus sequences (promoter elements) for more efficient initiation and transcription of downstream genes.

A "genetic fusion" according to this invention is a chimeric DNA containing a promoter and a coding sequence that are not associated in nature.

A "replicon" is any genetic element (e.g., plasmid, chromosome, virus) that functions as an autonomous unit of DNA replication in vivo; i.e., capable of replication under its own control.

Vectors are used to introduce a foreign substance, such as DNA, RNA or protein, into an organism. A "DNA vector" is a replicon, such as plasmid, phage or cosmid, to which another DNA segment may be attached so as to bring about the replication of the attached segment.

A cell has been "transformed" by exogenous DNA when such exogenous DNA has been introduced inside the cell wall. Exogenous DNA may or may not be integrated (covalently linked) to chromosomal DNA making up the genome of the cell. For example, the exogenous DNA may be maintained on an extrachromosomal element (or replicon) such as a plasmid. A stably transformed cell is one in which the exogenous DNA has become integrated into a chromosome so that it is inherited by daughter cells through chromosome replication. This stability is demonstrated by the ability of the cell to establish cell lines or clones comprised entirely of a population of daughter cells containing the exogenous DNA.

"Salt" as used in herein refers to an inorganic ionic compound which is commonly found in sea water or a mixture of such compounds. The concentration of salt is expressed herein as the amount of such compounds that provide the ionic equivalent to a given weight of sodium chloride. The salt concentration of seawater is about 32–33 g/L.

Transformation Systems

Transformed cells are produced by introducing exogenous DNA into a population of target cells and selecting the cells which have taken up the exogenous DNA, usually by measuring expression of some determinant present on the exogenous DNA but missing from the untransformed cells. Transformation of algae and marine organisms is complicated by lack of selection systems which are effective in salt water media. The difficulty is overcome in accordance with this invention by using zeocin resistance as a selective marker, because resistance to zeocin (and related antibiotics) has been discovered to be maintained in high salt medium to a much greater extent than is observed for other antibiotic resistance genes. Thus, transformants containing exogenous DNA with a zeocin resistance determinant will grow in salt water in the presence of suitable concentrations of zeocin, while untransformed cells of marine organisms will not.

This invention is provides improved methods for transformation of cells and selection of transformants from marine organisms, which may be multicelled marine organisms, including marine plants, or marine microorganisms. Marine microorganisms within the contemplation of this invention include marine bacteria, marine fungi, and marine algae, including marine diatoms. In a particular embodiement, this invention also contemplates use of the transformation system for transformation of halobacteria. Additionally, this invention provides particularly effective promoters for driving expression of foreign genes in cells of photosynthetic algae, including cells of marine algae.

The basic techniques used for transformation and expression in algal systems and marine organisms are the same as those commonly used for *Escherichia coli, Saccharomyces cerevisiae* and other species which are routinely transformed. Standard methods for construction of chimeric DNA and its use in transformation of cells are familiar to the skilled worker, and these methods have been described in a number to texts for standard molecular biological manipulation (see Packer & Glaser, 1988, "Cyanobacteria", *Meth. Enzymol.,* Vol. 167; Weissbach & Weissbach, 1988, "Methods for plant molecular biology," Academic Press, New York, Sambrook, Fritsch & Maniatis, 1989, *"Molecular*

Cloning: A laboratory manual," 2nd edition Cold Spring Harbor Laboratory Press, Cold Spring Harbor, N.Y.; and Clark M S, 1997, *Plant Molecular Biology*, Springer, N.Y.).

To summarize, the upstream DNA sequences of a gene expressed under control of a suitable promoter may be restriction mapped and areas important for the expression of the protein characterized. The exact location of the start codon of the gene is determined and, making use of this information and the restriction map, a vector may be designed for expression of a heterologous protein by removing the region responsible for encoding the gene's protein but leaving the upstream region found to contain the genetic material responsible for control of the gene's expression. A synthetic oligonucleotide is preferably inserted in the location where the protein sequence once was, such that any additional gene could be cloned in using restriction endonuclease sites in the synthetic oligonucleotide (i.e., a multicloning site). An unrelated gene (or coding sequence) inserted at this site would then be under the control of an extant start codon and upstream regulatory region that will drive expression of the foreign (i.e., not normally there) protein encoded by this gene. Once the gene for the foreign protein is put into a cloning vector, it can be introduced into the host organism using any of several methods, some of which might be particular to the host organism. Variations on these methods are amply described in the general literature references above. Manipulation of conditions to optimize transformation for a particular host is within the skill of the art.

Different promoters may be more or less effective in different host systems. For example, the promoter from a gene associated with photosynthesis in one photosynthetic species may be used to direct expression of a protein in transformed algal cells or cells of another photosynthetic marine organism. Suitable promoters may be isolated from or synthesized based on known sequences from other photosynthetic organisms. Preferred promoters are those for genes from other photosynthetic species, including other algae and cyanobacteria, which are homologous to the photosynthetic genes of the algal host to be transformed (see, e.g., Table 1). For a particular algal host, it may be preferable to identify the homologous light harvesting gene from that host and isolate the homologous promoter from the host organism to get optimal expression. However, it has been found for some organisms that foreign promoters give excellent or less restricted expression in the host relative to the homologous promoter of the host organism (Mermet-Bovier, et al., 1993, *Curr. Microbiol.*, 26:323–327).

A series of light harvesting promoters from the fucoxanthin chlorophyll binding proteins have now been identified and cloned from *Phaeodactylum tricornutum* by the present inventors (see Apt, et al. (1996) "Stable nuclear transformation of the diatom *Phaeodactyltum tricornutum*," *Mol Gen. Genet.* 252:572–579, incorporated herein by reference). The use of fcp promoters for transformation of algae, especially photosynthetic diatoms, is described herein.

Genetic fusion constructs according to the invention can be made using standard techniques. In a preferred embodiment, the promoter of an algal light harvesting protein, such as a chlorophyll binding protein's promoter, is positioned on the 5' or upstream side of a coding sequence whose expression is desired. Preferably a fucoxanthin chlorophyll binding protein promoter is used. Alternatively, a carotenoid chlorophyll binding protein promoter, such as that of peridinin chlorophyll binding protein, can be used. The promoter may come from any eukaryotic algae which has light harvesting protein complexes. For example, brown algae or diatoms may be the source of the promoter. In one particularly preferred embodiment, the *Phaeodactlyum tricornutum*, fcpA promoter is used. (Bhaya and Grossman (1993), "Characterization of gene clusters encoding the fucoxanthin chlorophyll proteins of the diatom *Phaeodactylum tricornutum*," *Nucleic Acids Research*, 21:4458–4464). In order to evaluate promoter strength in a particular alga, reporter genes can be linked to a promoter. The linked construct is inserted into the alga and the expression of the reporter is gauged. Any gene whose mRNA or protein product can be easily measured can be used.

Downstream or 3' of the light harvesting protein promoter are fused one or more additional protein coding sequences. Coding sequences for single proteins can be used, as well as coding sequences for fusions of two or more proteins. Thus both a selectable marker and another sequence which one desires to introduce may be introduced fused to and downstream of a single light harvesting protein promoter. Alternatively, two protein coding sequences can be introduced, each under the control of a light harvesting promoter located on a single molecule.

One particularly useful selectable marker which may be used is the Sh ble gene which encodes the bleomycin binding protein from *Streptoalloteichus hindustanus*. Zeocin and phleomycin have been found to be particularly potent in inhibition of the growth of eukaryotic algae, especially in the presence of high concentrations of salt, especially concentrations above 3 g/L. Typical salt concentrations in growth media for marine algae are between about 10 and about 35 g/L, and more preferably between about 15–34 g/L. (Sea water contains about 32 to 33 g/L of salt.) In addition, the Sh ble protein confers zeocin resistance on algal cells. Zeocin or phleomcyin or other related antibiotics can be used interchangeably for selection with this marker. Thus, the sh ble gene has been found to function as a resistance determinant in algae, and use of the sh ble gene on transforming DNA in combination with a zeocin or phleomycin-type selection affords a convenient selection for transformants of eukaryotic algae. This is particularly useful for diatoms.

In a particularly preferred configuration, the sh ble gene is regulated by a promoter of a chlorophyll binding protein. Suitable promoters include the fcpA, fcpB, fcpC, and fcpE promoters, as well as any lhc promoter. Other promoters that may be used in genetic fusion constructs for transforming cells of photosynthetic organisms are listed in Table 1. Additional suitable promoters for use with these and other marine organisms are listed in Table 2, and other suitable promoters which are apparent to the skilled worker may be used in the selection system of this invention.

TABLE 1

Light related promoters cyanobacterial genes (taken from Houmard, et al., 1988, Methods in Enzymol., vol. 167, Chap. 89)

| | |
|---|---|
| apcA | allophycocyanin α subunit |
| apcB | allophycocyanin β subunit |
| apcC | linker polypeptide |
| apcD | allophycocyanin B |
| apcE | anchor polypeptide |
| atpA | coupling factor subunits |
| atpB | coupling factor subunits |
| atpC | coupling factor subunits |
| atpD | coupling factor subunits |
| atpE | coupling factor subunits |
| cpcA | c-phycocyanin α subunit |
| cpcB | c-phycocyanin β subunit |
| cpcC | linker polypeptide |
| cpcE | linker polypeptide |
| cpcF | cpc accumulation factor |
| cpcG | linker polypeptide |
| cpcH2 | linker polypeptide |
| cpcH3 | linker polypeptide |
| cpcI2 | linker polypeptide |
| cpcI3 | linker polypeptide |
| cpeA | phycoerythrin α subunit |
| cpeB | phycoerythrin β subunit |
| cit | carotenoid-hinding protein |
| psaA | chl a binding protein photosystem I |
| psaB | chl a binding protein photosystem I |
| psbA1 | D1 protein of PSII |
| psbA2 | D1 protein of PSII |
| psbB | CP47 chl a binding protein PSII |
| psbC | CP43 chl a binding protein PSII |
| psbK | a small PSII component (PBB-K) (see Ikeuchi et al. (1991) "Cloning of the psbK gene from Synechocystis sp. PCC6803 and characterization of the photosystem II in mutants lacking PSII-K," J Biol. Chem. 266: 11111–11115.) |
| pbsC2 | CP43 induced on iron stress |
| psbD1 | D2 protein of PSII |
| psbD2 | D2 protein of PSII |
| psbE | cytochrome b-559 |
| psbF | cytochrome b-559 |
| psbI | cytochrome b-559 |
| psbJ | cytochrome b-559 |
| psaD | photosystem I subunit |
| psaE | photosystem I subunit |
| rbcL | ribulose-bisphosphate carboxylase large subunit |
| rbcS | ribulose-bisphosphate carboxylase small subunit |
| woxA | 33-kDa Mn-stabilizing protein of PSII |

Non-cyanobacterial genes

| | |
|---|---|
| fcpA | fucoxanthin chlorophyll binding protein |
| fcpB | fucoxanthin chlorophyll binding protein |
| fcpC | fucoxanthin chlorophyll binding protein |
| fcpE | fucoxanthin chlorophyll binding protein |
| lhc | light harvesting chlorophyll binding protein gene(s) | plus homologs of cyanobacterial genes, such as:

| | |
|---|---|
| oee-1 | oxygen evolving enhancer protein, see Mayfield et al. (1990) Proc. Natl. Acad. Sci. USA 87: 2087–2091 |
| rbcL | ribulose bisphospate oxygenase/carboxylase large subnit, see Blowers et al. (1989) "Studies on Chlamydomonas chloroplast transformation: Foreign DNA can be stably maintained in the chromosome". Plant Cell 1: 123–132; Blowers et al. (1990) "Transcriptional analysis of endogenous and foreign genes in chloroplast transformations of Chlamydomonas". Plant Cell 2: 1059–1070. |
| atpA | coupling factor subunit, see Blowers et al. (1990) Plant Cell 2: 1059–1070. |
| atpB | coupling factor subunit, see Blowers et al. (1990) Plant Cell 2: 1059–1070. |
| cabII-1 | a light-harvesting chlorophyll a/b binding protein gene that is light regulated Blakenship et al. (1992) "Expression of chimeric genes by the light-cabII-1 promoter in Chlamydomonas reinhardtii: A babI-I/nit1 gene functions as a dominant selectable marker in a /nit1-nit1- strain". Mol. Cell. Biol. 12: 5268–5279. Used an endogenous promoter to express a homologous gene in the same host (green algal). |

TABLE 2

Non-light harvesting related promoters already used in some algal systems:

The nopaline synthase promoter and polyadenylation sequences from the Ti plasmid of *Agrobacterium tumefaciens*. See Hall et al. (1993) "Expression of a foreign gene in *Chlamydomonas reinhardtii*". Gene 124: 75–81.

The promoter region of the tubB2 gene from *Chlamydomonas reinhardtii*. See Davies et al. (1992) "Expression of the arylsulfatase gene from the B2-tubulin promoter in *Chlamydomonas reinhardtii*". Nucl. Acids Res. 20: 2959–2965.

The PL promoter from bacteriophage λ. See Gruber et al. (1991). "*Escherichia coli* and *Anaycystis nidulans* plasmid shuttle vectors containing the P-L promoter from bacteriophagac lambda". Current Micro. 22: 15–20.

CaMV 35S promoter. See Jarvis et al. (1991). "Transient expression of firefly leuciferase in prototplasts of the green alga *Chlorella ellipsodea*". Current Genet. 19: 317–322.

The bacterial trp promoter. See Kawata et al. (1991). "Expression of salmon growth hormone in the cyanobacterium *Agmenellum quadruplicatum*. Biotechnol. Lett. 13: 851–856.

Other useful protein coding sequences which may be fused to the upstream promoter include resistance determinants for herbicides, heavy metals, high pH or salt. Other useful protein coding sequences for fusion are those for transport proteins for reduced carbon compounds. Thus amino acid, carboxylic acid, and sugar transport proteins, such as the hexose uptake protein (HUP) of *Chlorella kessleri*, may be used conveniently. In addition, glucose metabolism enzymes or other useful products made by the recipient or other donor organisms may be used. The genes for glucuronidase or green fluorescent protein can be used as reporter genes.

The genetic fusion of the present invention may be introduced into cells of marine organisms or eukaryotic algae alone or as part of a DNA vector. Suitable vectors for use in marine organisms or eukaryotic algae are known in the art and any such vector may be used. Even vectors which do not replicate in algae can be useful, if recombination between the vector and the genome occurs.

Any method for introduction of the fusion construct into marine organisms and algae may be used. However, one particularly preferred method involves the use of DNA-coated particle bombardment. Another useful method involves vigorous agitation in the presence of glass beads, which renders some of the algal cells permeable to nucleic acids.

The methods of the present invention are particularly useful for the modification of algae to render them more susceptible to labeling with compounds which are labeled with stable isotopes. For example, stable isotopically labeled amino acids, sugars, carboxylic acids, or other reduced carbon compounds can be used to label algae. However, often the uptake by the cells of these labeled compounds is inefficient. The practice of the present invention will allow enhancement of the uptake of these labeled compounds by producing transformed photosynthetic algae having increased levels of transporter proteins specific for particular reduced carbon compounds, thereby improving the permeability of the cells to these compounds. Incorporation of such labeled compounds into algal metabolites is useful for structural determinations of the metabolites.

Growth of algae in salt concentrations of between 10 and about 35 g/L is often necessary to maintain viability of non-habituated, salt water algae. Thus use of zeocin-type antibiotics for selection of transformants provides the art with a benefit, since the toxicity of other antibiotics decreases more rapidly with increasing salt concentration, and thus other antibiotic selections do not work in the presence of high salt. Zeocin-based selection is particularly useful to avoid the need to habituate algae to low salt concentrations, as well as to allow selection of algae which cannot be habituated. Furthermore, transformed algae produced according to the method of this invention may be fully adapted to growth in high salt media. Thus, this invention provides a method for production of desired proteins in high salt medium by culture of algal cells transformed according to this invention with DNA containing the coding sequence of the desired protein under the control of a suitable promoter. The desired proteins can be produced in cultures of algae grown under salt conditions more optimal for growth of the microbes and recovered by standard protein recovery methods suitable for the desired protein.

The following examples are provided for exemplification purposes only and are not intended to limit the scope of the invention.

EXAMPLES

Example 1. Antibiotic and herbicide sensitivities of *Phaeodactylum tricornutum*.

*Phaeodactylum tricornutum* was insensitive to most of the common antibiotics for which resistance genes are available, under the growth conditions utilized (Table 3). Some antibiotics such as puromycin and chloramphenicol required very high concentrations for cell death compared to other eukaryotic organisms and were thus not suitable for selection. No sensitivity was observed for any of the herbicides used in plant transformation even when used at 1000 times higher concentrations then needed to cause plant cell death. Only zeocin and phleomycin resulted in cell death at low concentrations. Zeocin was utilized for subsequent selection.

When the salt concentration in the medium was decreased, toxicity of the various antibiotics generally increased. In particular, G418, hygromycin, nourseothricin, and puromycin all show promise for selection of transformants under reduced salt conditions. Resistance genes for use in selections based on these antibiotics are available from the American Type Culture Collection or can be obtained from the original organisms (e.g., nourseothricin: nat, see Krugel et al., 1993, *Gene.* 127:127–131, and sat, see Tietze, et al., 1990, *Nucl. Acid Res.,* 18:1290; puromycin: pac, see Lecalle, et al., 1989, *Gene,* 79:375–380; hygromycin: hyg, see Gritz, et al., 1983, *Gene,* 25:179–188; G418: neo, see Gruber, et al., 1993, in Glick, et al., eds, "Methods in Plant Molecular Biology and Biotechnology," CRC Press, Boca Raton, pp. 89–119).

TABLE 3

Sensitivity of *P. tricornutum* to antibiotics and plant herbicides for which resistance genes are available.

| COMPOUND | GROWTH LEVEL | CONCENTRATION |
|---|---|---|
| Antibiotics | | |
| Neomycin | +[a] | 1 mg/ml |
| Kanamycin | + | 1 mg/ml |
| Gentamicin | + | 1 mg/ml |
| Streptomycin | + | 1 mg/ml |
| Spectinomycin | + | 1 mg/ml |
| G418 | + | 1 mg/ml |
| Hygromycin | + | 1 mg/ml |
| Nourseothricin | – | 250 ug/ml |
| Puromycin | – | 200 ug/ml |
| Chloramphenicol | – | 200 ug/ml |
| Erythromycin | – | 100 ug/ml |
| Zeocin | – | 50 ug/ml |
| Phleomycin | – | 50 ug/ml |
| Bleomycin | + | 50 ug/ml |
| Herbicides | | |
| Glyphosate | + | 50 ug/ml |
| Chlorosulfuron | + | 50 ug/ml |
| Sulfometron methyl | + | 50 ug/ml |
| Imazapyr | + | 50 ug/ml |
| Phosphotricin | + | 50 ug/ml |
| Bialaphos | + | 50 ug/ml |

[a]No growth (–) or significant growth (+), at the highest concentration used or required for cell death.
Culture Conditions: *Phaeodactylum tricornutum* Bohlin (University of Texas Culture Collection, strain 646) was grown at 24° C. with continuous illumination at 100 $\mu Em^{-2}s^{-1}$ on LDM media containing 1.2% agar. Liquid cultures were bubbled with air containing 1% $CO_2$ and grown in f/2 media, supplemented with 2 times the normal levels of nitrate and phosphate.

Example 2. Use of a zeocin resistance gene as a selective marker.

While demonstrating the use of a zeocin resistance gene as a selective marker, this example also demonstrates the use of a promoter for a chlorophyll binding protein to drive exogenous gene expression.

Zeocin is a member of the phleomycin family of structurally related antibiotics isolated from Streptomyces (Berdy (1980), "Bleomycin-Type Antibiotics". In: Berdy, J. (ed) *Handbook of Antibiotic Compounds. Vol. IV, Part L Amino acid and Peptide Antibiotics.* CRC Press, Boca Raton, Fl. pp. 459–497). These antibiotics are small glycopeptides that differ by their terminal amine residues and are commonly chelated to copper in commercial preparations. They are effective at low concentration against bacteria and a wide variety of eukaryotic organisms (a complete reference list of all known applications is available). The mode by which these antibiotics cause cell death involves binding to and cleavage of DNA.

The sh ble gene (400 bp) from the bacterium *Streptoalloteichus hindustanus* encodes the protein that confers resistance to zeocin and phleomycin (Drocourt et al., "Cassettes of the *Streptoalloteichus hindustanus* ble gene for transformation of lower and higher eukaryotes to phleomycin resistance". *Nucleic Acids Research* 18:4009 (1990)). The Sh ble protein (13 kDa) is a binding protein with a strong affinity for the phleomycin family of antibiotics. When zeocin is bound by the Sh ble protein it is no longer active in cleaving the cellular DNA. Upon introduction of this gene into *P. tricornutum* cells, it is possible to recover transformants that are able to grow on zeocin.

The promoter and terminator regions of the fcpA, B, C, and E genes of *P. tricornutum* were fused onto the sh ble gene (FIG. 1). The plasmid pfcpA was constructed by subcloning the fcpA PstIKpnI fragment (Bhaya and Grossman, 1993, supra) into Bluescript SK(Stratagene). The sh ble gene was PCR amplified from pUT362 (Cayla) using primers Ble-R5 (CTAGATATCAAGATGGCCAAGTTGACCAGT) (SEQ ID NO: 1), and Ble-H3 (GATAAGCTTCAGTCCTGCTCCTCGG) (SEQ ID NO: 2) which created EcoRV and HindIII sites at the 5' and 3' regions of the reading frame. The fcpA/ble gene fusion was constructed by inserting the sh ble PCR generated fragment between the EcoRV and HindIII sites of the fcpA gene. The entire 5' untranslated region of the resulting gene fusion was identical to the endogenous fcpA gene.

The plasmid containing the chimeric gene was used to coat tungsten particles which were bombarded into the cells. Super-coiled (S.C.) or linear plasmid DNA (cut with KpnI) from pfcp/ble was used for bombardments. Cells were bombarded using the BIO-RAD BIOLISTIC PDS-1000/HE™ particle delivery system fitted with 1,100, 1,350 or 1,500 psi rupture discs. Tungsten particles MS, M17 (0.4 or 1.1 $\mu$m median diameter, respectively) or gold particles (1.0 $\mu$m diameter) were coated with 0.8 $\mu$m plasmid DNA/bombardment using $CaCl_2$ and spermidine as described by the manufacturer. Approximately $5 \times 10^7$ cells were spread on LDM agar medium 1 hr prior to bombardment and positioned at various levels within the chamber (as indicated in Table 2) of the Biolistic device. Bombarded cells were illuminated for 48 hr prior to resuspension in sterile seawater and $5 \times 10^6$ cells were spread on fresh LDM agar medium containing 75 $\mu$g/ml Zeocin (In Vitrogen). The plates were placed under constant illumination (100 $\mu$tEm$^{-2}$ s$^{-1}$) for 2–3 weeks, after which resistant colonies were easily visible.

After 2 weeks on selective medium, resistant colonies were readily visible. Each colony was restreaked on selective medium containing 100, 250 and 500 $\mu$g/ml zeocin. Restreaked cells that grew were scored as resistant colonies. All primary resistant colonies grew on the three concentrations of zeocin.

The results obtained under different experimental conditions used for transformation are outlined in Table 4. The largest number of resistant colonies was obtained by placing the petri dishes containing cells at level two of the BIOLISTIC™ device. Only a small number of resistant colonies were obtained by placing the cells at level three. The size of the particles has a significant effect on the number of resistant colonies recovered, with the larger M17 tungsten particles (1.1 $\mu$m median diameter) being the best. Pressure effects were most pronounced with the smaller particles.

Higher frequencies of transformation were observed with supercoiled DNA versus linear DNA No resistant colonies were recovered or observed in the no DNA controls.

TABLE 4

Recovery of resistant colonies using different transformation conditions.

| Particle Size | DNA | Pressure (psi) | Chamber Height | Avg # of Colonies | Number of Plates |
|---|---|---|---|---|---|
| M17 | S.C. | 1,500 | 2 | 8.0 | n = 3 |
| M17 | S.C. | 1,500 | 3 | 1.5 | n = 2 |
| M17 | S.C. | 1,350 | 2 | 6.0 | n = 5 |
| M17 | S.C. | 1,100 | 2 | 6.6 | n = 3 |
| M17 | Linear | 1,350 | 2 | 0.2 | n = 5 |
| M5 | S.C. | 1,500 | 2 | 3.0 | n = 3 |
| M5 | S.C. | 1,500 | 3 | 0 | n = 2 |
| M5 | S.C. | 1,350 | 2 | 2.4 | n = 5 |
| MS | S.C. | 1,100 | 2 | 0 | n = 3 |
| M5 | Linear | 1,350 | 2 | 0 | n = 5 |
| AU1.0 | S.C. | 1,350 | 2 | 2.0 | n = 4 |
| M17 | None | 1,500 | 2 | 0 | n = 3 |
| M17 | None | 1,500 | 3 | 0 | n = 2 |
| M17 | None | 1,350 | 2 | 0 | n = 5 |
| M17 | None | 1,100 | 2 | 0 | n = 3 |
| MS | None | 1,500 | 2 | 0 | n = 3 |
| M5 | None | 1,500 | 3 | 0 | n = 2 |
| M5 | None | 1,350 | 2 | 0 | n = 5 |
| M5 | None | 1,100 | 2 | 0 | n = 3 |

Example 3. Molecular analysis of the algal transformants obtained.

To determine whether resistant colonies obtained by bombardment contained DNA sequences derived from plasmid pfcp/ble, the DNA from 7 isolates (A–G) was analyzed by hybridization to the entire pfcp/ble plasmid.

Figure 2:
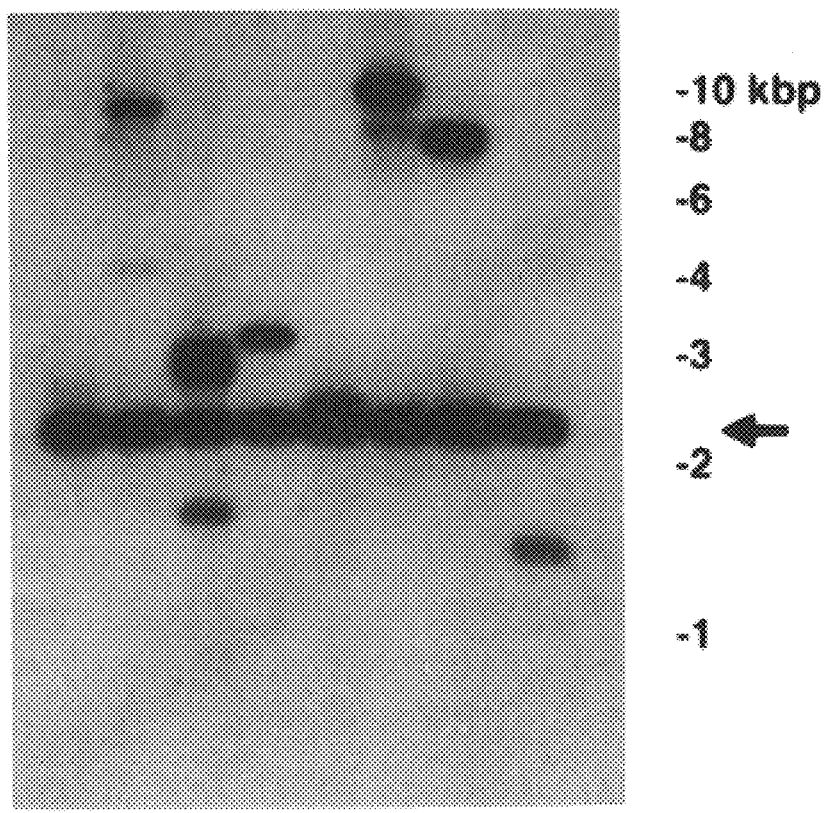
FIG. 2 shows the results of Southern analysis of seven *P. tricornutum* zeocin resistant strains (A–G). Total DNA was digested with BglII EcoRI or SalI to completion. The digested DNA was electrophoresed and blotted using standard procedures. The resulting DNA blot was probed with radioactive pfcp/ble. The hybridizing band containing the endogenous fcpA gene for each set of samples is marked by an arrow. Additional hybridizing bands indicate inserted copies of pfcp/ble into the genome. DNA from wild-type cells is not included on this blot.

Hybridization with pfcp/ble revealed that all the resistant P. triconutum strains examined contained multiple hybridizing bands (FIG. 2), not including the endogenous fcpA gene which also hybridizes to the plasmid. A single common hybridizing band was present in DNA from all of the transformants digested with a specific restriction enzyme (BglII, EcoRI or SalL marked by arrow). These bands correspond exactly in size to the endogenous fragment of the fcpA gene present in wild type cells (Bhaya and Grossman, 1993, supra). All the resistant strains had 1 or more additional hybridizing bands of various sizes, indicating the presence of one or more copies of pfcp/ble in their genome.

Figure 3:
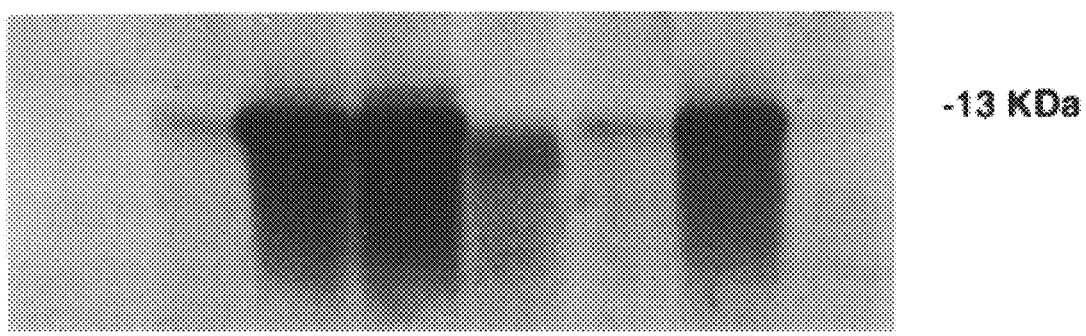
FIG. 3 shows the results of Western analysis of seven *P. tricornutum* zeocin-resistant strains (A–G). Total cellular protein (10 μg) was electrophoresed and immunoblotted using standard techniques. The resulting protein blot was probed with a rabbit polyclonal antibody to the Sh ble protein (Cayla) and visualized with an alkaline phosphatase anti-rabbit IgG conjugate.

As determined by immunoblots, the Sh ble protein was also present in all the resistant strains (A–G); it was undetectable in nontransformed cells (FIG. 3). The level of Sh ble protein determined immunologically was extremely variable, ranging from <1 ng to >20 ng/10 $\mu$g total cell protein.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

We claim:

1. A method of transforming cells of *P. tricornutum* comprising the steps of:
   introducing DNA into the cells, wherein the DNA contains a zeocin resistance determinant; and
   selecting for transformants by culturing the cells in a medium comprising a concentration of zeocin or phleomycin which is inhibitory to untransformed cells,
   wherein growth of the organism is enhanced by the presence of salt in the medium, and wherein the medium contains between 10 and 35 g/L salt.

2. A method of transforming cells of an organism selected from the group consisting of marine organisms and eukaryotic algae comprising the steps of:
   introducing DNA into the cells, wherein the DNA contains a zeocin resistance determinant; and
   selecting for transformants by culturing the cells in a medium comprising a concentration of zeocin or phleomycin which is inhibitory to untransformed,
   wherein the antibiotic resistance determinant is regulated by a light harvesting protein promoter.

3. The method of claim 2, wherein the light having protein is a chlorophyll binding protein.

4. The method of claim 3, wherein the chlorophyll binding protein is fucoxanthin chlorophyll binding protein.

5. A genetic fusion consisting of a promoter of a gene which encodes a photosynthetic algal light harvesting protein upstream from and fused to one or more protein coding sequences.

6. The genetic fusion of claim 5, wherein the light harvesting protein is a chlorophyll binding protein.

7. The genetic fusion of claim 6, wherein the chlorophyll binding protein is fucoxanthin chlorophyll binding protein.

8. The genetic fusion of claim 5, wherein expression of the protein coding sequence confers antibiotic resistance on algal cells.

9. The genetic fusion of claim 8, wherein the coding sequence which confers antibiotic resistance on algal cells encodes Sh ble.

10. The genetic fusion of claim 8, wherein expression of the protein coding sequence confers resistance to nourseothricin.

11. The genetic fusion of claim 5, wherein one of the protein coding sequences encodes a transporter protein of a reduced carbon compound.

12. The genetic fusion of claim 11, wherein the transporter protein is a carboxylic acid transporter protein.

13. The genetic fusion of claim 11, wherein the transporter protein is an amino acid transporter protein.

14. The genetic fusion of claim 11, wherein the transporter protein is a sugar transporter protein.

15. The genetic fusion of claim 14, wherein the transporter protein is a hexose transporter protein.

16. The genetic fusion of claim 15, wherein the transporter protein is a hexose uptake protein (HUP) of Chlorella.

17. The genetic fusion of claim 15, wherein the transporter protein is a hexose uptake protein (HUP) of *Chlorella kessleri*.

18. The genetic fusion of claim 5, wherein the light harvesting protein is from a diatom.

19. The genetic fusion of claim 18, wherein the light harvesting protein is from *Phaeodactylum tricornutum*.

20. A DNA vector comprising the genetic fusion of any one of claims 5, 8, 11, 12, 13, or 17.

21. An algal cell transformed with the DNA vector of claim 20.

22. A method of producing a recombinant protein comprising culture of an algal cell transformed with a genetic fusion according to any one of claims 5, 8, 11, 12, 13, or 17, wherein the genetic fusion further contains a coding sequence encoding the recombinant protein under control of a promoter which functions in the algal cell.

* * * * *